United States Patent [19]

Ruderian

[11] Patent Number: 4,587,959

[45] Date of Patent: May 13, 1986

[54] HOT AND COLD THERAPEUTIC APPLICATOR

[76] Inventor: Max J. Ruderian, 545 Hanley Ave., Los Angeles, Calif. 90049

[21] Appl. No.: 719,063

[22] Filed: Apr. 2, 1985

[51] Int. Cl.$^4$ .................... A61F 7/00; A61M 37/00

[52] U.S. Cl. .................... 128/24.1; 128/400; 604/24; 604/291; 34/67

[58] Field of Search .................... 128/24.1, 399, 400; 604/23, 24, 289, 290, 291; 62/293; 126/204; 34/67

[56] References Cited

U.S. PATENT DOCUMENTS 2,739,586 3/1956 Preis .................... 128/24.1
3,132,688 5/1964 Nowak .................... 126/204 X
3,168,895 2/1965 Okuhara .................... 128/399

FOREIGN PATENT DOCUMENTS 797686 1/1981 U.S.S.R. .................... 128/399

*Primary Examiner*—Anton O. Oechsle
*Attorney, Agent, or Firm*—Pastoriza, Kelly & Lowry

[57] ABSTRACT

A single casing houses first and second blowers for expelling air through first and second outlet passages. One of the outlet passages incorporates a heater so that hot air can be expelled. The other passage is free of any heater so that cool air is expelled from the second passage. By alternately actuating the blowers, a person can be treated to hot air and then cool air.

7 Claims, 2 Drawing Figures

HOT AND COLD THERAPEUTIC APPLICATOR

FIELD OF THE INVENTION

This invention relates generally to therapeutic devices and more particularly to a therapeutic applicator in which both hot and cool air can be provided from a single unit.

BACKGROUND OF THE INVENTION

In my co-pending Patent applications identified as follows:

Ser. No. 06/701,745 filed 2-14-85 for SALVE APPLICATOR;

Ser. No. 06/702,800 filed 2-19-85 for MASSAGING DEVICE;

there are disclosed various therapeutic devices in the form of massaging units wherein heated air is passed through an applicator surface to a person's skin while massaging is taking place. Vibrating means may constitute an integral part of the applicator as well as means for supplying a medicant to the applicator surface.

I have found that in addition to the excellent therapeutic results realizable by the various units described in the above applications, treatment of an area with heated air and thereafter cool air and then again with heated air and then again with cool air can also provide very beneficial results. This hot-cold application is similar to treatments wherein a person will enter a hot sauna and then a cool pool and then back into a hot sauna. Usually the heat is applied about one and one-half times as long as the cool air is applied.

To the best of my knowledge, there is presently no massaging unit or therapeutic device available which can provide for a hot and cold therapeutic treatment.

BRIEF DESCRIPTION OF THE PRESENT INVENTION

With the foregoing in mind, the present invention contemplates the provision of a therapeutic applicator in which hot and cold air can be applied during a massaging operation in an alternate manner and by a single unit.

More particularly, the present invention constitutes a casing having air entrance opening means and first and second air exit passages. A partition in the interior of the casing separates the first and second air exit passages and first and second blowers for directing incoming air along these air exit passages respectively are provided. Also, an air heating means in only one of the passages is provided. First and second switches on the casing permit operating the first and second blowers individually and at will whereby hot air only can be expelled from the first passage; cool air only can be expelled from the second passage; and hot and cool air can be simultaneously respectively expelled from the first and second passages if desired.

In a preferred embodiment, there is provided a third switch for operating the air heating means so that the air heating means can be turned off and cool air can be expelled alone from the first passage or simultaneously with cool air passing from the second passage.

BRIEF DESCRIPTION OF THE DRAWINGS

A better understanding of this invention as well as further features and advantages thereof will be had by now referring to the accompanying drawings in which.

DETAILED DESCRIPTION OF THE PREFERRED EMBODIMENT

Figure 1:
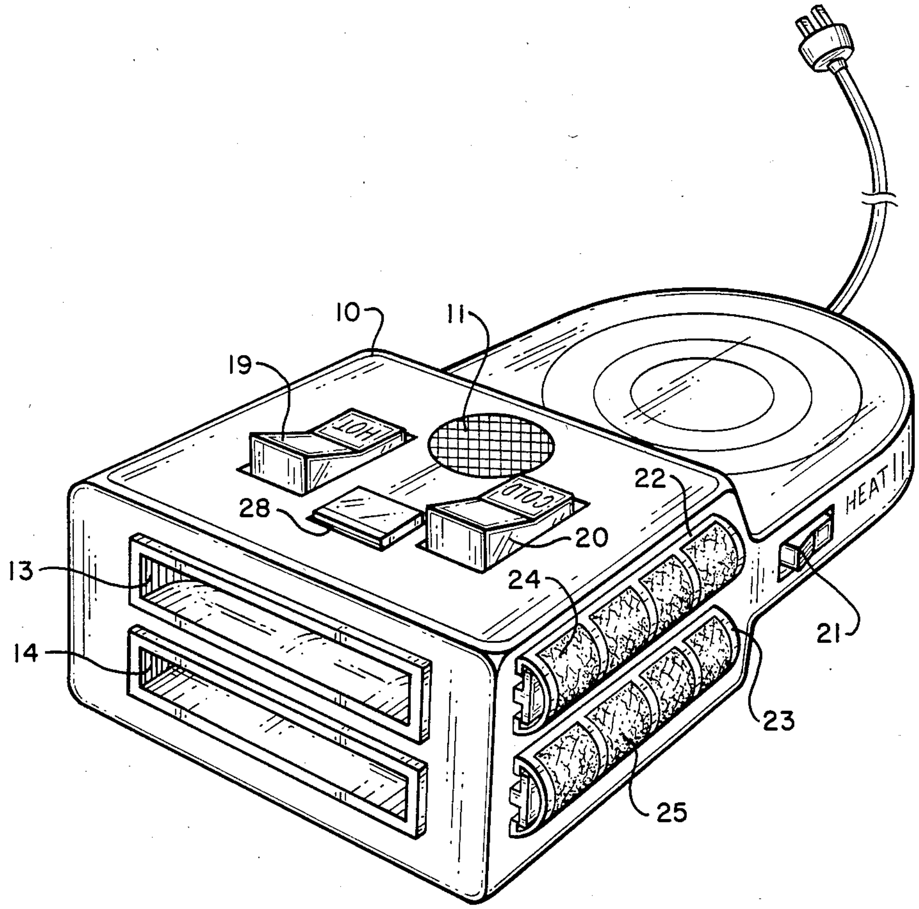
FIG. 1 is a perspective view of the hot and cold therapeutic applicator of this invention; and, FIG. 2 is a side elevational view broken away and partly in cross section illustrating the interior features of the applicator of FIG. 1.
Figure 2:
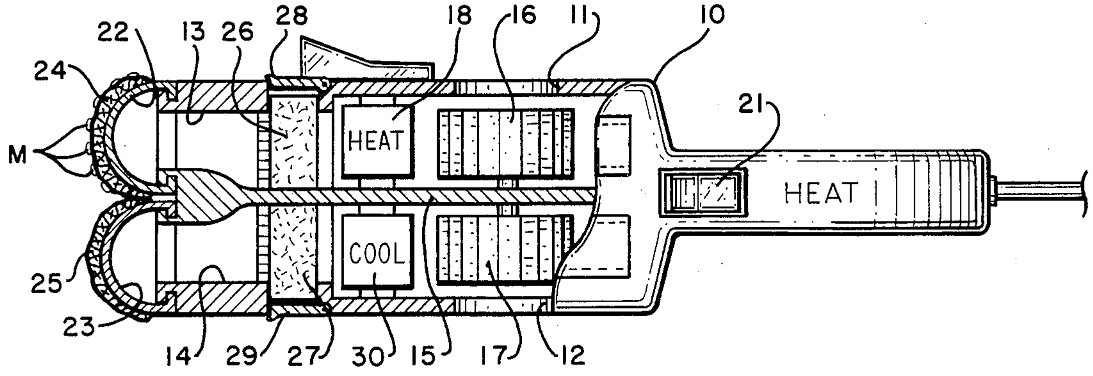

Referring to both FIGS. 1 and 2 together, the applicator comprises a casing 10 having air entrance opening means in the form of first and second individual air entrance openings 11 and 12, the air entrance opening 12 being disposed on the under side of the casing as seen in FIG. 2. Casing 10 further includes first and second air exit passages 13 and 14.

As best seen in FIG. 2, the interior of the casing 10 includes a partition 15 separating the first and second air exit passages 13 and 14. First and second blowers 16 and 17, in turn, are provided in these passages for directing incoming air along the first and second air exit passages respectively. An air heating means 18 is provided only in the first passage 13 as shown.

Referring back to FIG. 1, there are provided first and second switches 19 and 20 for respectively operating the first and second blowers.

With the foregoing arrangement, hot air only can be expelled from the first passage; cool air only can be expelled from the second passage; and hot and cool air can be simultaneously respectively expelled from the first and second passages if desired. In addition, there may be provided a third switch 21 shown on the side of the casing 10 in both FIGS. 1 and 2 for operating the air heating means 18 whereby the air heating means can be turned off so that cool air can be expelled alone from the passage 13 or simultaneously with cool air passing from the second passage 14.

As shown in both FIGS. 1 and 2, there are provided first and second frame means 22 and 23 which can be moved from positions on the side of the casing as shown in FIG. 1 to positions in front of the first and second air exit passages respectively as shown in FIG. 2. Fabric materials 24 and 25 are provided on each of these frames respectively to provide a cushioned surface for engaging the skin of a person's body. A medicant M can be provided in at least one of the fabric materials such as the fabric material 24 on the first frame 22.

Still referring to FIG. 2, within the first and second passages 13 and 14 there may be provided other means shown at 26 and 27 for adding first and second ingredients to the air flow exiting from the passages respectively. For example, the means 26 might constitute a sponge saturated with water thereby providing moisture or water vapor to the heated air passing through the first air exit passage 13. The sponge is held in place by suitable screening material as indicated.

The second means 27 in the second passage for cool air, might include an ingredient such as menthol thereby enhancing the cooling sensation of the exiting air.

Appropriate access doors may be provided for the removal and replacement of these first and second means such as indicated at 28 and 29 respectively.

In operation, a person could apply first the hot air flow from the first passage 13 through the frame at 22, fabric 24 and any medicant that might be in the fabric to a skin area to be massaged. The heated air might be applied for a minute and one-half or so. Thereafter, the operator will simply turn off the first blower and turn on the second blower to provide cool air from the second passage 14. The same area of the skin previously massaged with heated air can now be treated with the cool air. Preferably the cool air would be applied for perhaps only a minute or so. In other words, the application of heat is normally about one and one-half times as long as the application of the cool air.

After the cool air has been applied, the user can again apply heat to the same area or move on to another area of the body.

In some instances, it might be desirable simply to provide heat on an area of the body and then alternately apply a cooling effect. In this instance, the frame members and corresponding fabric materials can be stored on the side of the casing 10 as illustrated in FIG. 1 and hot air from the first passage 13 applied directly to the skin area. Thereafter, the switch 19 is operated to turn off the blower for the hot air and switch 20 operated to turn on the blower for the cool air which would then be applied over the same skin area.

It will be noted in FIG. 2 that there is provided a means indicated by the block 30 and marked "COOL" for effecting a cooling of the air flow through the second passage. This means 30 can be electrically operated to cool the air flow therethrough and is shown simply to illustrate that further cooling can be effected if desired.

From all of the foregoing, it will be evident that the present invention has provided a very versatile therapeutic applicator wherein hot and cold treatments can be alternately applied to provide further therapeutic benefits.

I claim:

1. A hot and cold therapeutic applicator including, in combination:

(a) a casing having air entrance opening means and first and second air exit passages;

(b) a partition in the interior of said casing separating said first and second air exit passages;

(c) first and second blowers for directing incoming air along said first and second air exit passages respectively;

(d) air heating means only in said first passage; and (e) first and second switches for respectively operating said first and second blowers whereby hot air only can be expelled from said first passage; cool air only can be expelled from said second passage; and hot and cool air can be simultaneously respectively expelled from said first and second passages.

2. An applicator according to claim 1, including a third switch for operating said air heating means whereby said air heating means can be turned off so that cool air can be expelled alone from said first passage or simultaneously with cool air passing from said second passage.

3. An applicator according to claim 1, in which said air entrance opening means include first and second individual air entrance openings for passing air to said first and second blowers respectively.

4. An applicator according to claim 1, including first and second frame means movable from positions on the side of said casing to positions in front of said first and second air exit passages respectively; fabric materials on each of said frames respectively to provide a cushioned surface for engaging the skin of a person's body; and a medicant in at least one of said fabric materials.

5. An applicator according to claim 1, including first and second means in said first and second passages for adding first and second ingredients to the air flow exiting from the passages, respectively.

6. An applicator according to claim 5, in which one of said ingredients is water vapor.

7. An applicator according to claim 5, in which said first ingredient is water vapor and said second ingredient is menthol.

* * * * *